(12) United States Patent
Wu et al.

(10) Patent No.: US 10,765,629 B2
(45) Date of Patent: Sep. 8, 2020

(54) SOLID COMPLEX, PREPARATIONS AND USES THEREOF

(71) Applicant: Allergan, Inc., Irvine, CA (US)

(72) Inventors: Ke Wu, Irvine, CA (US); Evgenyi Shalaev, Dana Point, CA (US); Prem Swaroop Mohanty, Irvine, CA (US); Jinping Wan, Irvine, CA (US)

(73) Assignee: ALLERGAN, INC., Irvine, CA (US)

(*) Notice: Subject to any disclaimer, the term of this patent is extended or adjusted under 35 U.S.C. 154(b) by 0 days.

(21) Appl. No.: 16/634,072

(22) PCT Filed: Jul. 24, 2018

(86) PCT No.: PCT/US2018/043456
§ 371 (c)(1),
(2) Date: Jan. 24, 2020

(87) PCT Pub. No.: WO2019/023211
PCT Pub. Date: Jan. 31, 2019

(65) Prior Publication Data
US 2020/0170941 A1 Jun. 4, 2020

Related U.S. Application Data

(60) Provisional application No. 62/536,846, filed on Jul. 25, 2017.

(51) Int. Cl.
*A61K 9/00* (2006.01)
*A61K 47/40* (2006.01)
*A61K 47/34* (2017.01)

(52) U.S. Cl.
CPC .......... *A61K 9/0051* (2013.01); *A61K 9/0024* (2013.01); *A61K 47/34* (2013.01); *A61K 47/40* (2013.01)

(58) Field of Classification Search
None
See application file for complete search history.

(56) References Cited

U.S. PATENT DOCUMENTS

| 6,602,900 B2 * | 8/2003 | Burk ............... A61K 31/381 514/365 |
| 6,933,289 B2 * | 8/2005 | Lyons ............. A61K 9/0048 424/488 |
| 2005/0004074 A1 | 1/2005 | Lyons et al. |
| 2014/0271780 A1 | 9/2014 | Hughes et al. |

FOREIGN PATENT DOCUMENTS

| WO | WO 2009/007828 A1 * | 1/2009 | ............ C08B 37/08 |
| WO | WO 2015/089475 A1 * | 6/2015 | ............ C07D 333/28 |

OTHER PUBLICATIONS

Rodriguez-Aller et al., Euuropean Journal of Pharmaceutics and Biopharmaceutics (2015), vol. 95, Part B, pp. 203-214.*
Cross et al, Rules for the Nomenclature of Organic Chemistry, Pure & Appli. Chem, 1976, 11-30, vol. 45.
Del Valle, E.M.M., Cyclodextrins and their uses: a review, Process Biochem., 2004, 1033-1046, 39.
Heinrich Stahl, Pharmaceutical Salts, Handbook of Pharmaceutical Salts, 2002, 329-345, International Union of Pure and Applied Chemistry, Verlag Helvetica Chemica Acta—Zürich.
PCT International Search Report & Wriitten Opinion dated Nov. 2, 2018, for PCT/US2018/043456 filed Jul. 24, 2018, in the name of Allergan, Inc.

* cited by examiner

*Primary Examiner* — Brian J Davis
(74) *Attorney, Agent, or Firm* — Jonathan Bass

(57) ABSTRACT

Described herein is a solid complex comprising (Z)-7-((1R, 2R,3R,5S)-2-((S,E)-5-(2,5-dichlorothiophen-3-yl)-3-hydroxypent-1-en-1-yl)-3,5-dihydroxycyclopentyl)hept-5-enamide (hereinafter "Compound 1") and γ-cyclodextrin, and preparations and uses thereof. Also described herein are certain solid forms, preparations and uses thereof.

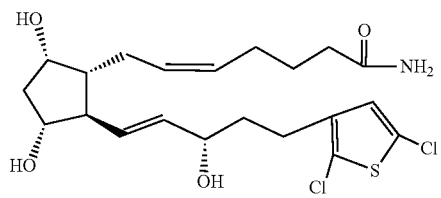

16 Claims, 15 Drawing Sheets

SOLID COMPLEX, PREPARATIONS AND USES THEREOF

CROSS-REFERENCE TO RELATED APPLICATIONS

This application is a national stage entry under 35 USC 371 of international application PCT/US2018/043456, filed Jul. 24, 2018, which claims priority to and/or the benefit of U.S. provisional application 62/536,846, filed Jul. 25, 2017, which is hereby incorporated by reference herein in its entirety.

TECHNICAL FIELD

The subject matter disclosed herein relates to a solid complex, preparations and uses thereof, and in particular to a solid complex comprising (Z)-7-((1R,2R,3R,5 S)-2-((S,E)-5-(2,5-dichlorothiophen-3-yl)-3-hydroxypent-1-en-1-yl)-3,5-dihydroxycyclopentyl)hept-5-enamide (hereinafter "Compound 1") and γ-cyclodextrin and preparations and uses thereof.

BACKGROUND

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupillary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical β-adrenoreceptor antagonists have traditionally been the drugs of choice for treating glaucoma.

In addition, the ability of a compound to exist in more than one crystalline structure or form is known as polymorphism. Many compounds may exist unexpectedly as polymorph crystals and those compounds may also exist in a solid amorphous state. However, the current knowledge and understanding of polymorphism is still such that there is no reasonable degree of predictability with respect to what crystalline forms of the compound might exist and how to make possible unknown polymorphs or other crystalline forms.

Solid state forms of compounds, crystalline or amorphous forms, can be analyzed by one or more solid state analytical methods. Those methods include, for example, X-ray powder diffraction, differential scanning calorimetry, and thermogravimetric analysis.

The solid state forms may be characterized according to X-ray powder diffraction. However, it is known in the art that the measured peaks in the X-ray powder diffractogram of a solid form may vary, because of, for example, different experimental conditions and/or preferred orientations. And according to the instrument precision, the measurement error of 2θ value is generally at ±0.2° (2θ). Moreover, relative intensities have been recognized as non-characteristic for a particular solid form (See Bhattacharya et al., "Polymorphism in Pharmaceutical Solids," p. 334, 2009.)

Therefore, there is a need for compounds, such as the complex comprising (Z)-7-((1R,2R,3R,5 S)-2-((S,E)-5-(2,5-dichlorothiophen-3-yl)-3-hydroxypent-1-en-1-yl)-3,5-dihydroxycyclopentyl)hept-5-enamide (hereinafter "Compound 1") and γ-cyclodextrin described herein, for the treatment of ophthalmic diseases such as glaucoma, and for related compositions and methods.

SUMMARY

Disclosed is a complex comprising Compound 1 and γ-cyclodextrin (hereinafter "Solid Complex").

Also disclosed is a pharmaceutical composition, comprising the Solid Complex and a pharmaceutically acceptable excipient.

Also disclosed is a method of preparing a pharmaceutical composition, comprising combining the Solid Complex, with a pharmaceutically acceptable excipient.

Also disclosed is a method of treating glaucoma, comprising administering to a patient in need thereof a therapeutically effective amount of the Solid Complex or a pharmaceutical composition comprising or made from the Solid Complex.

Some example embodiments are listed below.

Example Embodiment 1

A solid complex of (Z)-7-((1R,2R,3R,5S)-2-((S,E)-5-(2,5-dichlorothiophen-3-yl)-3-hydroxypent-1-en-1-yl)-3,5-dihydroxycyclopentyl)hept-5-enamide with γ-cyclodextrin.

Example Embodiment 2

The solid complex of example embodiment 1, which is crystalline.

Example Embodiment 3

The solid complex of example embodiment 2, which has an XRPD pattern with peaks at 7.58, 10.68, 14.33, 16.82, 23.82, 26.89, 28.51, 30.06, and 35.13, each of the diffraction angles being ±0.2 degrees (2θ).

Example Embodiment 4

The solid complex of example embodiment 1, which has an XRPD pattern with peaks at 10.83, 11.72, 12.36, 14.51, 19.42, 20.56, and 26.80, each of the diffraction angles being ±0.2 degrees (2θ).

Example Embodiment 5

The solid complex of example embodiment 1, which is amorphous.

Example Embodiment 6

The solid complex of any of example embodiments 1-5, wherein the molar ratio of (Z)-7-((1R,2R,3R,5S)-2-((S,E)-5-(2,5-dichlorothiophen-3-yl)-3-hydroxypent-1-en-1-yl)-3,5-dihydroxycyclopentyl)hept-5-enamide versus γ-cyclodextrin is about 1:1.

Example Embodiment 7

A pharmaceutical composition comprising the solid complex of any of example embodiments 1-6 and a pharmaceutically acceptable excipient.

Example Embodiment 8

The pharmaceutical composition of example embodiment 7, which is in the form of an intraocular implant.

Example Embodiment 9

The pharmaceutical composition of example embodiment 8, wherein the intraocular implant comprises a biodegradable polymer and the solid complex of any of example embodiments 1-8.

Example Embodiment 10

The pharmaceutical composition of example embodiment 9, wherein the biodegradable polymer is a homo- or copolymer of D-lactic acid, L-lactic acid, racemic lactic acid, glycolic acid, caprolactone, and combinations thereof.

Example Embodiment 11

The pharmaceutical composition of example embodiment 9 or 10, wherein the biodegradable polymer is a random copolymer of 50/50 PLGA.

Example Embodiment 12

A method of preparing a pharmaceutical composition comprising combining the solid complex of any of example embodiment 1-6 with one or more pharmaceutically acceptable excipients.

Example Embodiment 13

The method of example embodiment 12, wherein the pharmaceutical composition is in the form of a solution for ophthalmic application.

Example Embodiment 14

The method of example embodiment 12, wherein the pharmaceutical composition is a solid implant.

Example Embodiment 15

The method of example embodiment 12, wherein the method further comprises subjecting the combination of the solid complex and one or more pharmaceutically acceptable excipients to hot-melt extrusion.

Example Embodiment 16

The method of example embodiment 15, wherein the pharmaceutical composition is a solid implant.

BRIEF DESCRIPTION OF DRAWING

FIG. 2C' shows TGA/DSC of the Solid Complex obtained from Example 3.

DETAILED DESCRIPTION

Definitions

Figure 1A:
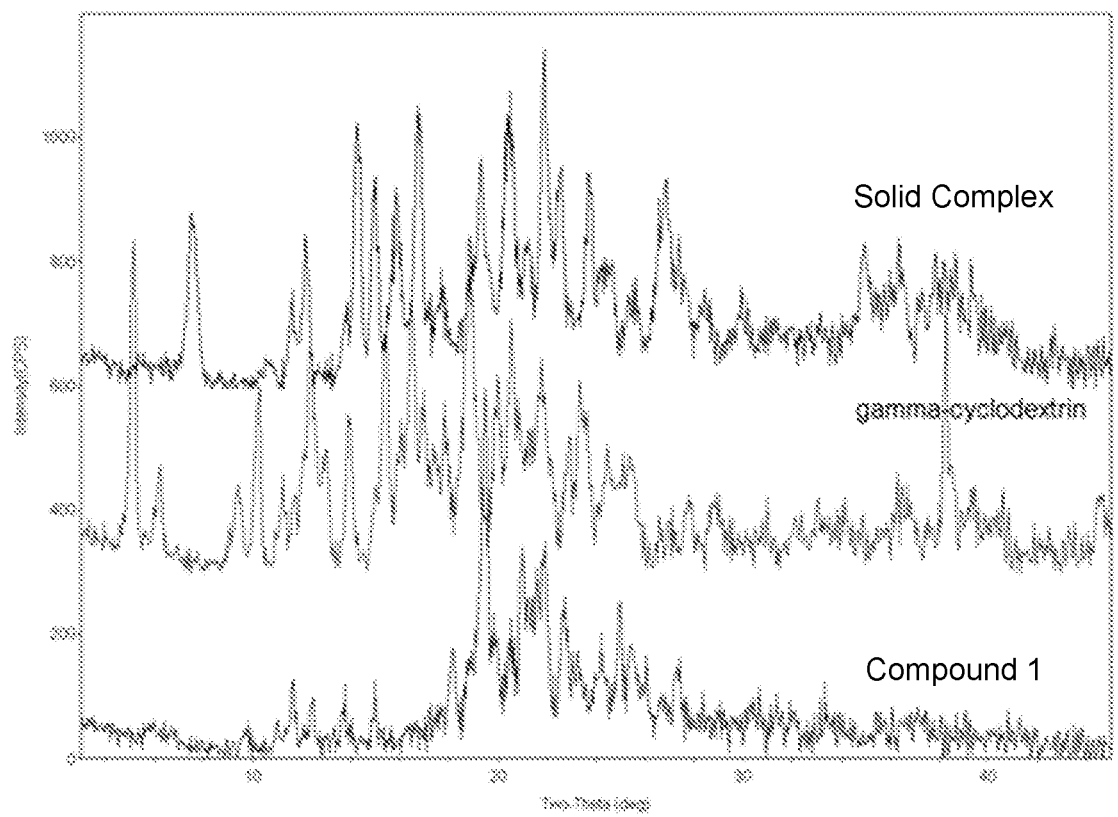
FIG. 1A shows Overlay of X-Ray Powder Diffractions (XRPDs) of the Solid Complex obtained from Example 1, γ-cyclodextrin, and Compound 1.

Various aspects now will be described more fully hereinafter. Such aspects may, however, be embodied in many different forms and should not be construed as limited to the embodiments set forth herein; rather, these embodiments are provided so that this disclosure will be thorough and complete, and will fully convey its scope to those skilled in the art.

For convenience, certain terms employed in the specification, examples and claims are collected here. Unless defined otherwise, all technical and scientific terms used in this disclosure have the same meanings as commonly understood by one of ordinary skill in the art to which this disclosure belongs.

Unless otherwise indicated, "a" or "an", such as in a pharmaceutically acceptable excipient, means one or more.

The term "about" when used in connection with a value or range means the deviation is within 5% of a given value, or within 5% of lower and upper limit of a given range.

"Biodegradable polymer" means a polymer or polymers which degrade in vivo, and wherein erosion of the polymer or polymers occurs concurrent with or subsequent to release of the therapeutic agent. A biodegradable polymer may be a homopolymer, a copolymer, or a polymer comprising more than two different polymeric units. The polymer can be a gel or hydrogel type polymer, poly lactic acid or poly(lactic-co-glycolic) acid or polyethylene glycolpolymer or mixtures or derivatives thereof.

A "pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. "A pharmaceutically acceptable excipient" as used in the specification and claims includes both one and more than one such excipient. Exemplary pharmaceutically acceptable excipient can be pharmaceutically acceptable polymers, preservatives, surfactants, antioxidants, and stabilizers, etc.

An "intraocular implant" refers to a device or element that is configured to be placed in the eye. Examples include extruded filaments, comprising a biodegradable polymer material and a pharmaceutically active agent, such as the Solid Complex described herein associated with the polymer material, and cut to a length suitable for placement in an eye. Intraocular implants are generally biocompatible with the physiological conditions of an eye and do not cause adverse reactions in the eye. In certain forms of the present invention, an intraocular implant may be sized and formulated for placement in the anterior chamber or vitreous body of the eye. Intraocular implants may be placed in an eye without significantly disrupting vision of the eye. Intraocular implants comprising one or more biodegradable polymers and the Solid Complex described herein are examples of an intraocular implant (drug delivery system) within the scope of the present invention.

Solid Complex

Disclosed herein is a solid complex comprising (Z)-7-((1R,2R,3R,5S)-2-((S,E)-5-(2,5-dichlorothiophen-3-yl)-3-hydroxypent-1-en-1-yl)-3,5-dihydroxycyclopentyl)hept-5-enamide (hereinafter "Compound 1") and γ-cyclodextrin.

Compound 1 has the structure below:

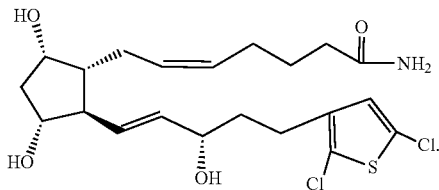 [SMILES: NC(=O)CCC/C=C\C[C@@H]1[C@@H](/C=C/[C@@H](O)CCc2cc(Cl)sc2Cl)[C@H](O)C[C@@H]1O]

The synthesis of compound 1 is described in WO1996/036599.

Two crystalline forms of non-complexed Compound 1, namely an anhydrous form (Form A) and a hemihydrate (Form B) have been identified (see, WO2015/089475). Both forms have a low melting temperature (less than 50° C.). The solid drug substance converts to an amorphous oil when formulated as a polymeric implant via hot melt extrusion (HME, typically around 60-120° C.). The amorphous form is thermodynamically unstable, which increases risk of physical and chemical instability during storage. Therefore, a solid form with a better thermal stability (i.e., a higher melting point or glass transition temperature) is highly desired.

The Solid Complex can be prepared by mixing Compound 1 and γ-cyclodextrin in water to form a suspension and collecting the resulting solid. In the Solid Complex, Compound 1 and γ-cyclodextrin may form non-covalent bonds.

Figure 3A:
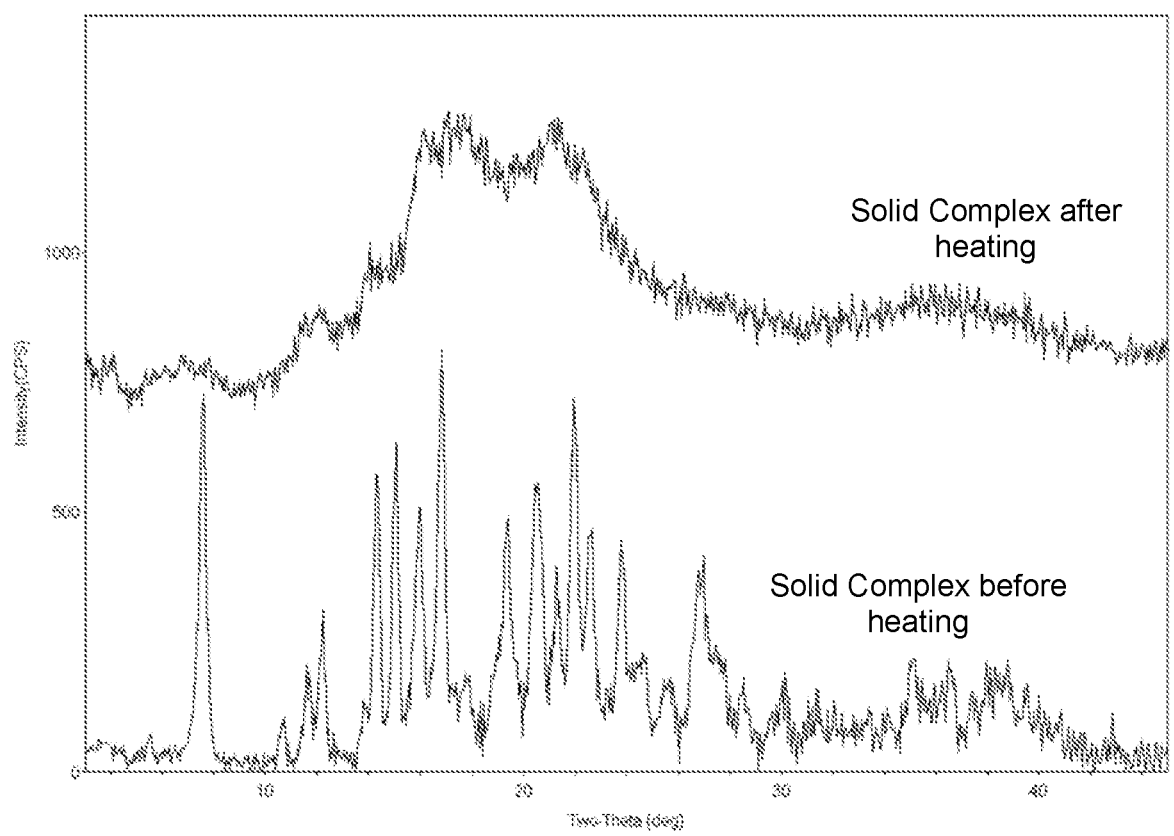
FIG. 3A shows XRPDs of the Solid Complex obtained in Example 1 before and after being heated to 150° C. at 10° C./min.
Figure 7:
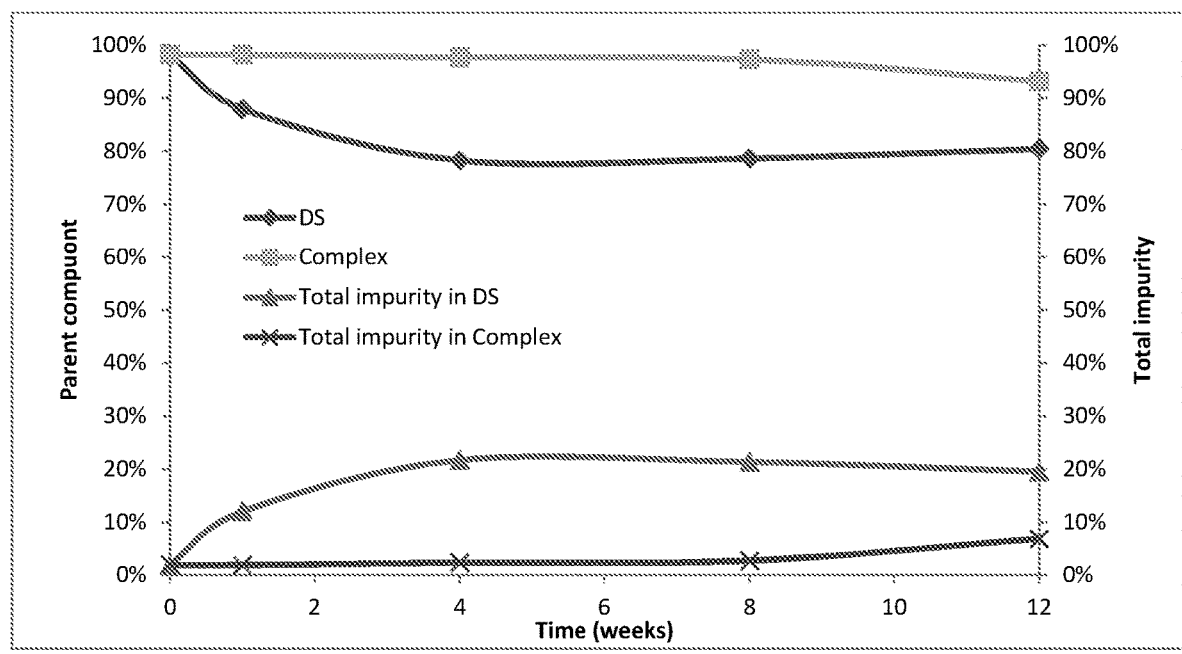
FIG. 7 shows Time Profile of Compound 1 Potency and Total Impurity (DS Refers to Compound 1 and Complex refers to the Solid Complex obtained from Example 1.)

The isolated Solid Complex turns into amorphous but remains solid after being heated to 150° C. (FIG. 3A; see Example 1). The Solid Complex remains solid after 12 weeks of exposure to 40° C./75% RH while the individual drug substance turns into oil within hours under the same storage condition (see Example 2). In addition, superior chemical stability of the Solid Complex is also observed under the same storage condition. This is represented by the significantly slower potency loss and gentler growth of impurities (FIG. 7; see Example 2). The Solid Complex hence has properties that are more amenable to manufacturing an implant by HME compared to Compound 1 alone.

Figure 1B:
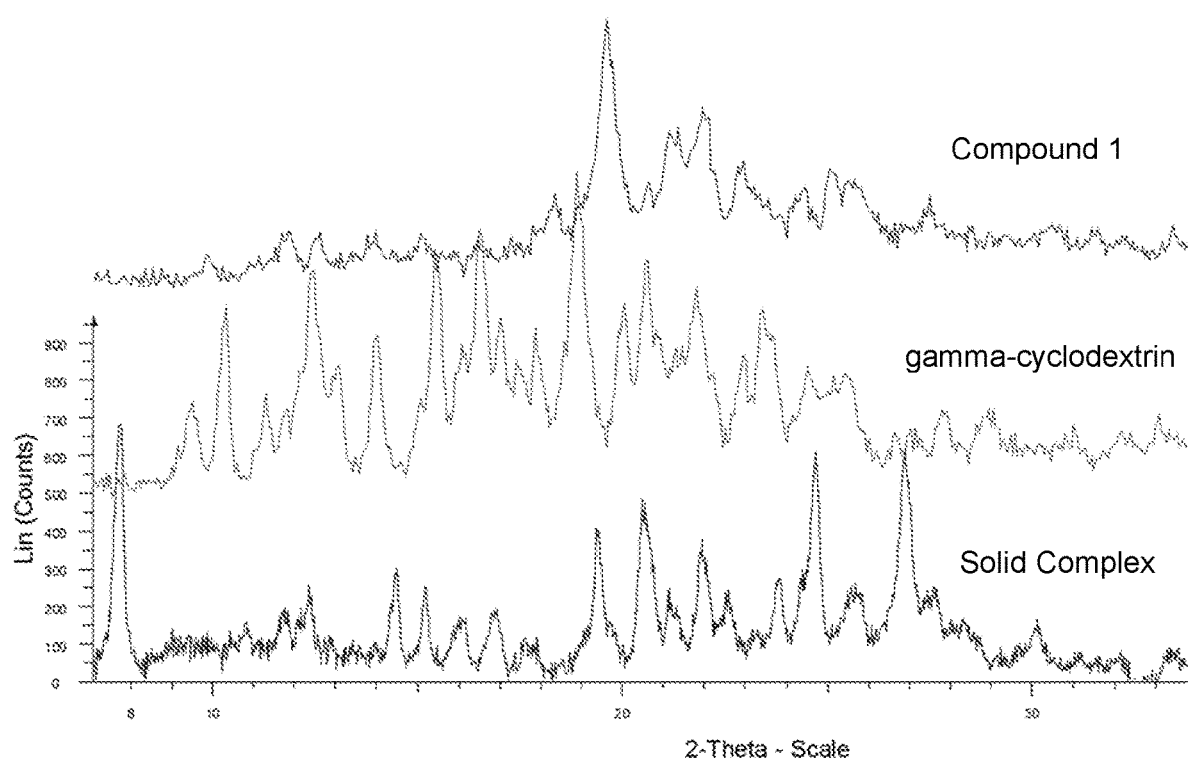
FIG. 1B shows Overlay of XRPDs of the Solid Complex obtained from Example 3, γ-cyclodextrin, and Compound 1.
Figure 10:
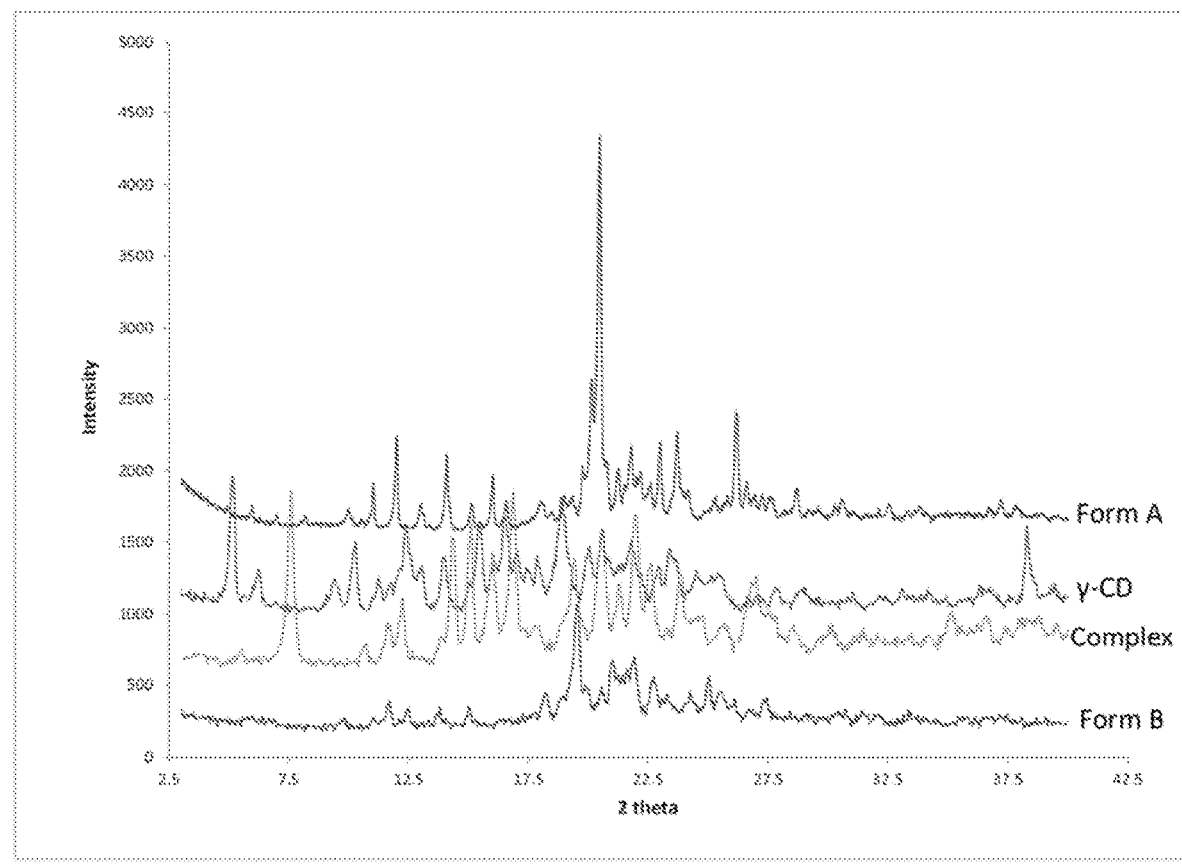
FIG. 10 shows an overlay of XRPD patterns of uncomplexed compound 1 (Form A and Form B), gamma cyclodextrin (γ-CD), and the Solid Complex.

In some embodiments, the XRPD of the Solid Complex as described herein may have peaks (2θ) chosen from those having the following values: 7.58, 14.33, and 23.82, each of the diffraction angles being ±0.2 degrees (2θ). In some embodiments, the XRPD of the Solid Complex as described herein may have peaks (2θ) chosen from those having the following values: 10.68, 16.82, and 26.89, each of the diffraction angles being ±0.2 degrees (2θ). In some embodiments, the XRPD of the Solid Complex as described herein may have peaks (2θ) chosen from those having the following values: 28.51, 30.06, and 35.13, each of the diffraction angles being ±0.2 degrees (2θ). In some embodiments, the XRPD of the Solid Complex as described herein may have peaks (2θ) chosen from those having the following values: 7.58, 10.68, 14.33, and 16.82, each of the diffraction angles being ±0.2 degrees (2θ). In some embodiments, the XRPD of the Solid Complex as described herein may have peaks (2θ) chosen from those having the following values: 7.58, 10.68, 14.33, 16.82, 23.82, 26.89, and 28.51, each of the diffraction angles being ±0.2 degrees (2θ). In some embodiments, the XRPD of the Solid Complex as described herein may have peaks (2θ) chosen from those having the following values: 7.58, 10.68, 14.33, 16.82, 23.82, 26.89, 28.51, 30.06, and 35.13, each of the diffraction angles being ±0.2 degrees (2θ). In some embodiments, the XRPD of the Solid Complex as described herein may have peaks (2θ) chosen from those having the following values: 10.83, 11.72, 12.36, 14.51, 19.42, 20.56, and 26.80, each of the diffraction angles being ±0.2 degrees (2θ). In some embodiments, the Solid Complex as described herein may have a XRPD substantially similar to that shown in FIGS. 1A and 1B for the Solid Complex obtained in Example 1 and Example 3, respectively, and also to that shown in FIG. 10 for the Solid Complex obtained in Example 1. "Substantially similarity" exists between one XRPD and another XRPD when the majority of peaks (such as more than 80% of peaks) in the range of 0 to 40 2θ degrees of the one XRPD can find corresponding peaks in the other XRPD (within +0.2 degrees 2θ) even if corresponding relative intensities of peaks differ.

Figure 2A:
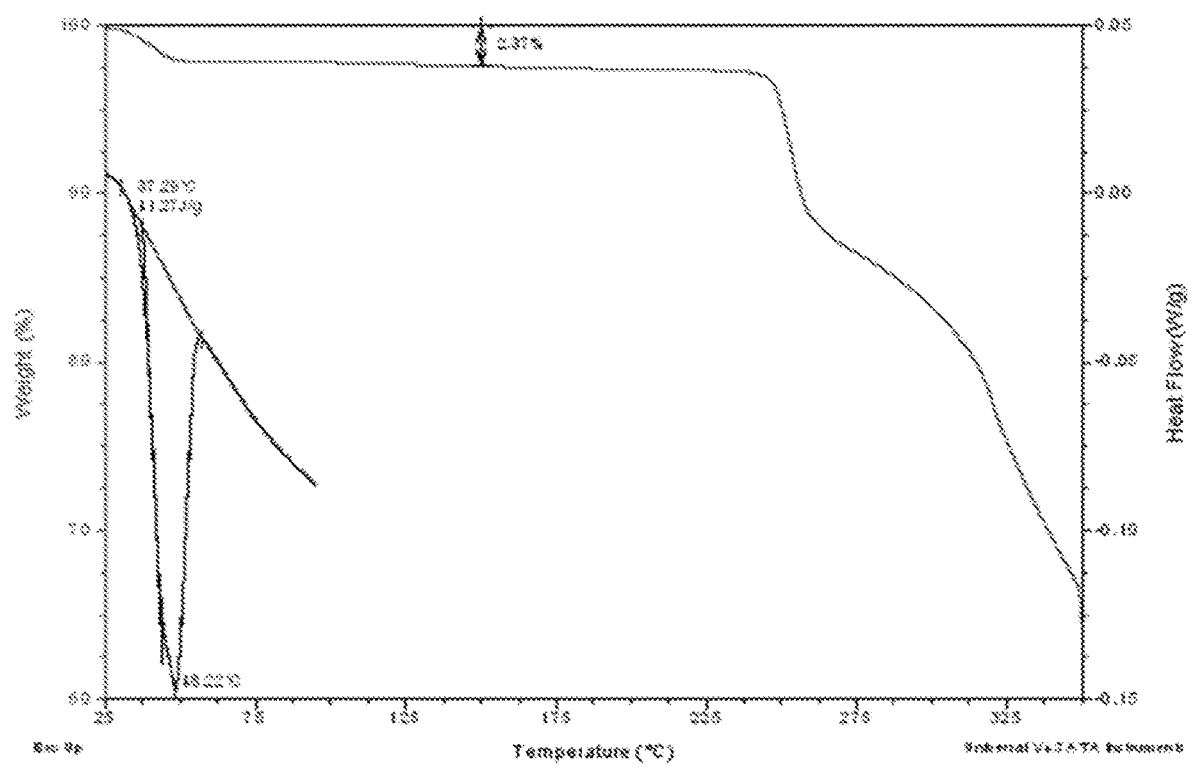
FIG. 2A shows thermogravimetric analysis/differential scanning calorimetry (TGA/DSC) of Compound 1.
Figure 2B:
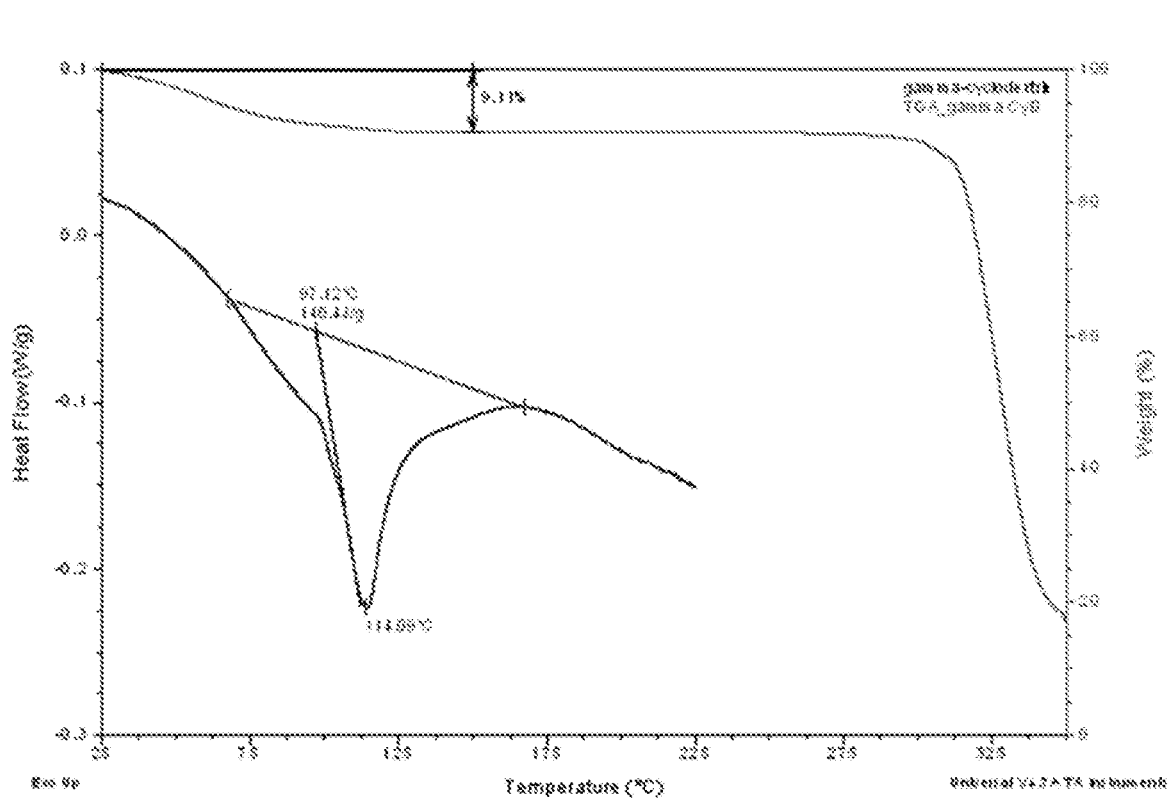
FIG. 2B shows TGA/DSC of gamma-cyclodextrin.
Figure 2C:
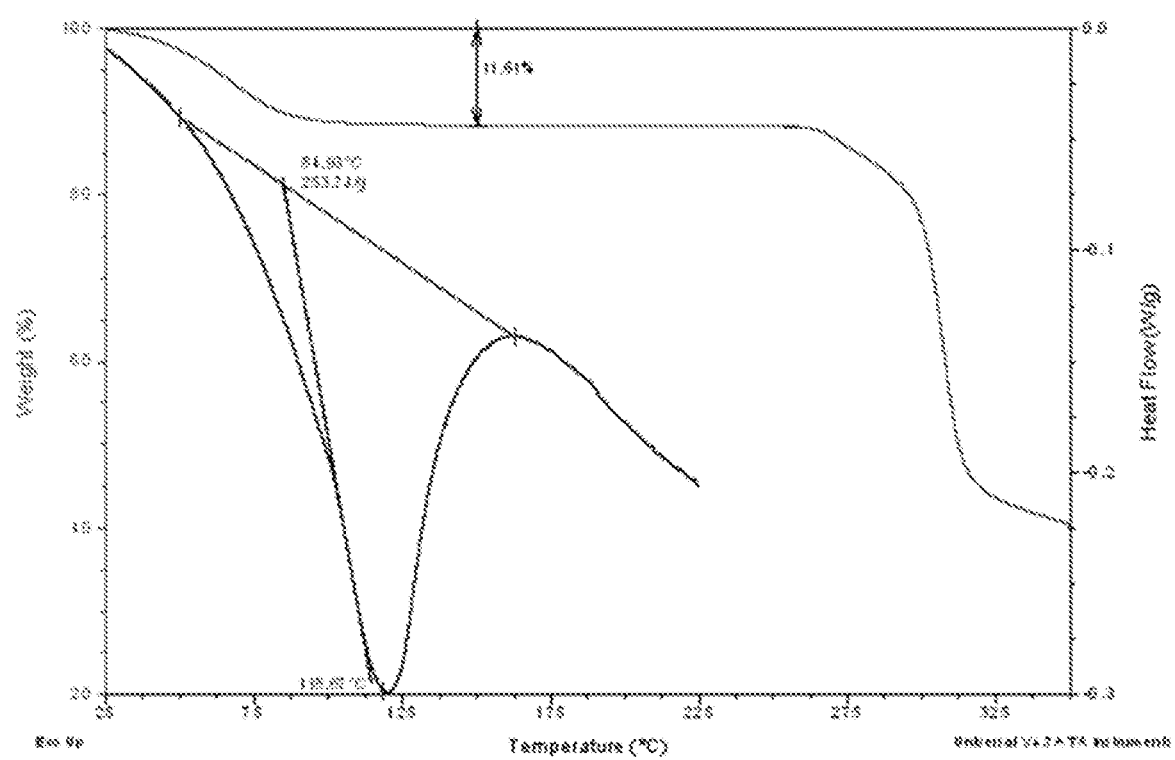
FIG. 2C shows TGA/DSC of the Solid Complex obtained from Example 1.
Figure 2C:
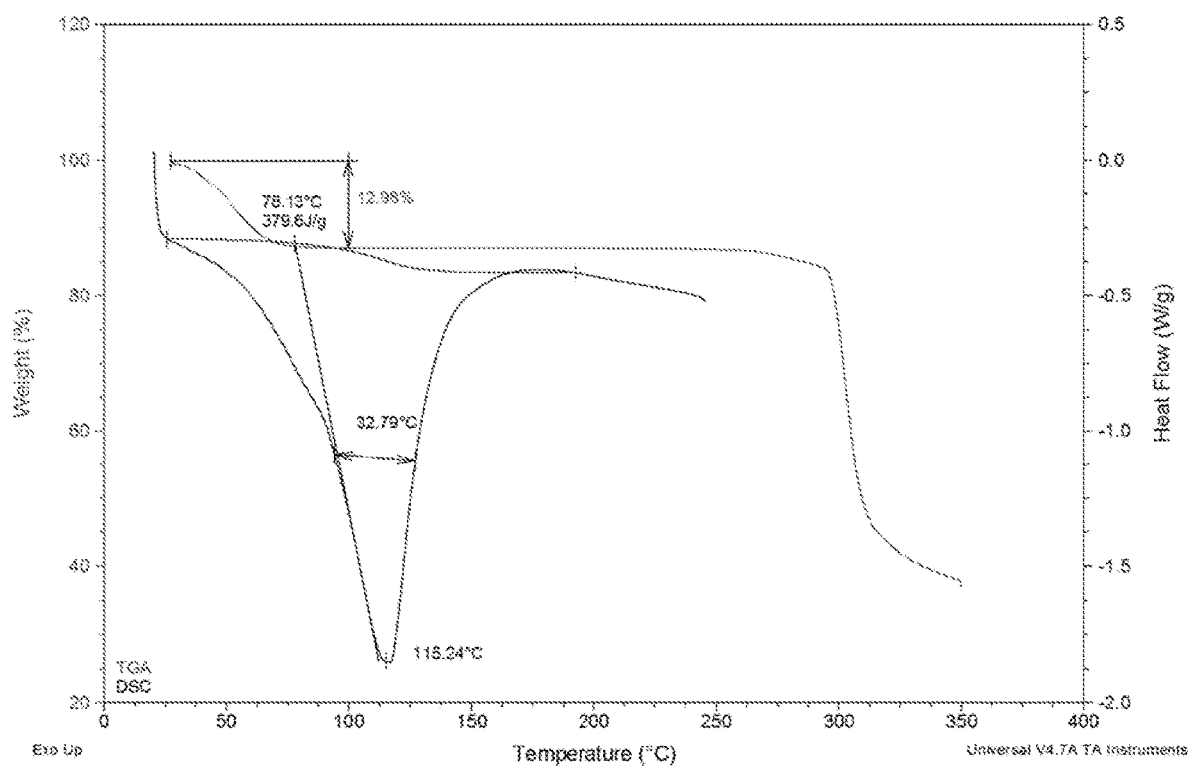

In some embodiments, the Solid Complex may be characterized according to differential scanning calorimetry (DSC). For example, provided is an embodiment of the Solid Complex as described herein having a DSC substantially similar to that shown in FIGS. 2C and 2C'.

In some embodiments, the Solid Complex may be characterized by thermogravimetric analysis (TGA). For example, provided is an embodiment of the Solid Complex as described herein having a TGA indicating the Solid Complex as described herein as hydrous or anhydrous. See FIGS. 2C, 2C' and 4.

The Solid Complex showed a lower equilibrium solubility than Compound 1, rendering its potential for development as extended release system. On the other hand, other cyclodextrins such as alpha, beta, or hydroxypropyl-beta-cyclodextrin tend to form soluble complex in the solution.

Without wishing to be bound by theory, the inventors believe that the molar ratio of Compound 1 to γ-cyclodextrin in the Solid Complex is about 1:1.

Pharmaceutical Compositions

Provided is a method of preparing a pharmaceutical composition comprising combining the Solid Complex with a pharmaceutically acceptable excipient.

Also provided is a pharmaceutical composition, comprising the Solid Complex and a pharmaceutically acceptable excipient.

In some embodiments of the pharmaceutical composition, the pharmaceutical composition is in the form of an implant, such as an intracameral implant. In some embodiments of the pharmaceutical composition, the implant is for ocular use. In some embodiments of the pharmaceutical composition, the implant comprises the Solid Complex and a biodegradable polymer.

For example, in some embodiments, biodegradable implants that are sized and formulated for placement in the eye of a patient (intraocular implants) and that are made with the Solid Complex, dispersed in a biodegradable polymer material (or matrix) may be useful for reducing intraocular pressure and treating glaucoma. Biodegradable implants are a safe, non-toxic, and effective means by which to administer this compound to the anterior chamber.

An implant may have a size suitable for insertion, placement or implantation in an ocular region or site, such as the anterior chamber, posterior chamber, or vitreous body of the eye. The size of an implant may affect the rate of release, period of treatment, and concentration of the active agent in treated tissue. At equal active agent loads, larger implants may deliver a proportionately larger dose.

For example, an implant sized for placement in the anterior chamber (an intracameral implant) will generally have a diameter (or other dimension as appropriate for non-cylindrical filaments) of from 100 to 400 μm and a length of from 0.5 to 6 mm. The implants may generally be formed by a single or double extrusion process, may be cylindrical or non-cylindrical, and may have a total weight ranging from 10 μg to 500 μg. The weight may depend, in part, on the dosage desired. In some embodiments, implants suitable for placement in the anterior chamber of an eye and suitable for use according to the invention will have a diameter of between 100 μm and 300 μm, a length of between 0.5 mm and 2 mm, and a total weight of between 10 μg and 200 μg or between 10 μg and 100 μg. In some instances, the intracameral implant for reducing IOP has a total weight of from 10 μg to 100 μg, or more specifically from 30-100 μg. One embodiment is an extruded biodegradable intraocular implant that is suitable for placement in the anterior chamber of an eye and that is about 200 μm in diameter and about 1.5 mm in length.

The eye(s) in some patients suffering from glaucoma or more generally ocular hypertension may be more receptive to placement of the biodegradable implant in the vitreous body of the eye. The vitreous body may accept larger implants of the same general formulation. For example, an intravitreal implant may have a length of 1 mm to 10 mm, a diameter of 0.5 mm to 1.5 mm, and a total weight of 50 μg to 5000 μg. The implant may be scaled up or down depending on the site of administration in the eye and the size or the vitreous volume of the patient. While in most cases a single implant may be found to reduce intraocular pressure in an eye for a sustained period (e.g., at least 3 months), in some instances, the practitioner may find it useful to place two or more of the presently described implants in an ocular region of the eye to improve the therapeutic effect.

Regarding configuration, intraocular implants may be in the form of extruded rods or in the form of non-cylindrical filaments, having the dimensions described above. Wafers, sheets, or films and in some cases compressed tablets may also find use according to the present invention.

In general, an implant according to the present invention will comprise or consist of a biodegradable polymer material and be made using the Solid Complex. The polymer material may comprise or consist of one, two, three, or more biodegradable polymers, and optionally one or more excipients to further improve the stability and/or release characteristics of the implant.

The biodegradable polymer can be, for example, polymers of hydroxyaliphatic carboxylic acids, either homo- or copolymers, and polysaccharides. Included among the polyesters of interest are homo- or copolymers of D-lactic acid, L-lactic acid, racemic lactic acid, glycolic acid, caprolactone, and combinations thereof. Further examples of useful biodegradable polymers include polylactide polymers and poly(lactide-co-glycolide) copolymers. In some embodiments, the biodegradable polymer material may comprise a polylactide, a poly(lactide-co-glycolide), a mixture of two or more polylactide polymers (e.g., first and second polylactide polymers), a mixture of two or more poly(lactide-co-glycolide) copolymers, or a mixture of polylactide and poly(lactide-co-glycolide) polymers In particular forms of any of these implants, the polylactide polymer may be a poly(D,L-lactide) and the poly(lactide-co-glycolide) copolymer may be a poly(D,L-lactide-co-glycolide). In any of the aforementioned combinations, the two or more polymers may differ, one from the other, on the basis of their end group, repeating unit, inherent viscosity, or any combination thereof. Polylactide and poly(lactide-co-glycolide) polymers used in the present implants may have either a carboxyl (—COOH) or ester end group. In addition, two or more poly(lactide-co-glycolide) polymers may differ one from the other by the lactide:glycolide ratio in each polymer, which may vary from about 85:15 to about 50:50 to about 75:25, depending on the polymer. Copolymers of glycolic and lactic acid are of particular interest, where the rate of biodegradation is controlled by the ratio of glycolic to lactic acid. The percent of each monomer in poly(lactic-co-glycolic)acid (PLGA) copolymer may be 0-100%, about 15-85%, about 25-75%, or about 35-65%. For example, a 50/50 PLGA copolymer is used. Further for example, a random copolymer of 50/50 PLGA is used.

Poly(D,L-lactide) or PLA may be identified by CAS Number 26680-10-4 and may be represented as:

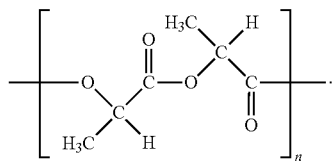

Poly(D,L-lactide-co-glycolide) or PLGA may be identified by CAS Number 26780-50-7 and may be represented as:

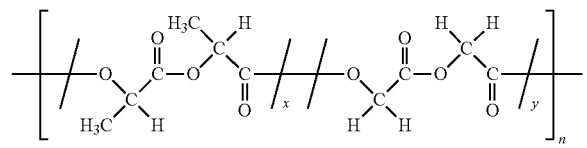

wherein x is the number of D,L-lactide repeat units and y is the number of glycolide repeat units, and n is the number of D,L-lactide-co-glycolide repeat units. Thus, poly(D,L-lactide-co-glycolide) (or PLGA) comprises one or more blocks of D,L-lactide repeat units and one or more blocks of glycolide repeat units, where the size and number of the respective blocks may vary.

The molar percent of each monomer or repeat unit in a PLGA copolymer may be 0-100%, about 15-85%, about 25-75%, or about 35-65%. In some embodiments, the D,L-lactide may be about 50% to about 75%, about 48% to about 52%, or about 50%; about 73% to about 77%, or about 75% of the PLGA polymer on a molar basis. The balance of the polymer may essentially be glycolide repeat units. For example, glycolide may be about 25% to about 50%, about 23% to about 27%, or about 25%; about 48% to about 52%, or about 50% of the PLGA polymer on a molar basis. Other groups, such as terminal or capping groups (end group) may be present in small amounts. As described above, in some embodiments, PLGA copolymers are used in conjunction with PLA polymers. In some implants, a 75/25 PLGA polymer having an ester end group is used.

The hydrophilic or hydrophobic character of the end groups may be useful in varying polymer material degradation. Polymers with a hydrophilic end group may degrade faster than polymers with a hydrophobic end group because a hydrophilic group may take up water. Examples of suitable hydrophilic end groups include, but are not limited to, carboxyl (acid end group), hydroxyl, and polyethylene glycol. These groups may be introduced by using an appropriate initiator. End groups may also be introduced after polymerization is complete to convert the terminal hydroxyl groups into other end groups. For example, ethylene oxide may convert hydroxyl to polyethylene glycol. Hydrophobic ended (also referred to as capped or end-capped) polymers have an ester linkage hydrophobic in nature at the polymer terminus.

Other polymers of interest include or may be selected from hydroxyaliphatic carboxylic acids, either homopolymers or copolymers, hyaluronic acid, sodium hyaluronate, polycaprolactones, polysaccharides, polyethers, calcium alginate, celluloses, carboxymethyl cellulose, polyvinyl alcohol, polyesters and combinations thereof.

Useful polysaccharides may include, without limitation, calcium alginate, and functionalized celluloses, such as carboxymethylcellulose esters characterized by being water insoluble, and having a molecular weight of about 5 kD to 500 kD, for example.

Release of a drug from a biodegradable polymer material is the consequence of several mechanisms or combinations of mechanisms. Some of these mechanisms include desorption from the implant's surface, dissolution, diffusion through porous channels of the hydrated polymer and erosion of the polymer(s) that make up the matrix. Erosion can be bulk or surface or a combination of both. The polymer matrix may release the therapeutic agent at a rate effective to sustain release of an amount of the agent (for example, Compound 1 and/or the gamma-CD complex of compound 1) for more than one month, for 1-3 months, for 3-6 months, or for 6 months after implantation into an eye. For example, the polymer material (or matrix) of the implant may degrade at a rate effective to sustain release of a therapeutically effective amount of the agent for one, two, three, or 6 month(s) in vitro or after being placed in an eye, or, more specifically, after being placed in the anterior chamber the eye.

The one or more biodegradable polymers used to form the matrix (polymer material of the implant) are desirably subject to enzymatic or hydrolytic instability. Additional preferred characteristics of the polymer(s) include biocompatibility, compatibility with the therapeutic component, ease of use of the polymer in making the implant of the present invention, a half-life in the physiological environment of at least about 6 hours, preferably greater than about one day, and water insolubility.

A biodegradable polymer material preferably degrades in vivo in a manner that provides for release of a therapeutically effective amount of the therapeutic agent for a period that is significantly greater than the in vivo life of the agent when administered in an eye drop formulation. As previously discussed, a polymer material may be a single polymer or copolymer, or, in some instances, a combination or blend of biodegradable polymers and/or copolymers.

In addition to the biodegradable polymer(s) and the therapeutic agent, an intraocular implant according to this invention may comprise one or more excipients to improve the stability (e.g., shelf life) of the therapeutic agent in the final implant, the ease of manufacture and handling of the implant, and/or the release characteristics of the implant. Un-complexed Compound 1, for example, is susceptible to oxidative degradation under various manufacturing, formulation, and storage conditions. The main degradation product is believed to be the C-15 ketone.

Examples of excipients for any of these purposes may include preservatives, antioxidants, buffering agents, chelating agents, electrolytes, or other excipients. In general, the excipient, when present, may constitute 0.001 to 10% or up to 15% by weight of the implant, and may be selected from any of those named below.

Useful water soluble preservatives may include sodium bisulfite, sodium bisulfate, sodium thiosulfate, benzalkonium chloride, chlorobutanol, thimerosal, phenylmercuric acetate, phenylmercuric nitrate, methylparaben, benzyl alcohol, polyvinyl alcohol and phenylethyl alcohol.

Suitable water soluble buffering agents are alkali or alkaline earth carbonates, phosphates, bicarbonates, citrates, borates, acetates, succinates, and the like, such as sodium phosphate, citrate, borate, acetate bicarbonate, and carbonate. These agents may be present in amounts sufficient to maintain a pH of a hydrated implant of between 2 to 9 and preferably 4 to 8. As such the buffering agent may be as much as 5% on a weight to weight basis of the total composition.

Suitable electrolytes may include sodium chloride, potassium chloride, and the like, including $MgCl_2$. Zinc salts may also be of interest.

Examples of antioxidants include ascorbate, ascorbic acid, L-ascorbic acid, melatonin, butylated hydroxyanisole, thiols, polyphenols, tocopherols such as alpha-tocopherol, mannitol, reduced glutathione, various carotenoids, cysteine, uric acid, taurine, tyrosine, superoxide dismutase, lutein, zeaxanthin, cryptoxanthin, astaxanthin, lycopene, N-acetylcysteine, carnosine, gamma-glutamylcysteine, quercitin, lactoferrin, dihydrolipoic acid, citrate, Ginkgo Biloba extract, tea catechins, bilberry extract, vitamin E or an ester of vitamin E, retinyl palmitate, and derivatives thereof.

Useful chelating agents may be selected from, for example, ethylenediaminetetraacetic acid (EDTA), ethylenediamine, porphine, and vitamin B-12.

Other excipients may include alcohols such as, for example, hexadecanol (also referred to as cetyl alcohol and hexadecan-1-ol, and sometimes denoted as C16-OH). In some embodiments, the implant may comprise a straight chain or branched alcohol that is greater than 10 carbons in length.

In one embodiment, an implant may further include polyethylene glycol such as for example polyethylene glycol 3350 (PEG 3350). In other embodiments, the implant does not contain PEG 3350.

An implant may include a combination of two or more of the above-named excipients.

The amount of biodegradable polymer material, and therefore the ratio and/or amount of the particular biodegradable polymer(s) used in an implant may vary depending on the Compound used and the release characteristics desired. A linear or constant, or nearly constant rate of release over a sustained period may be useful for the steady, long term (>1 month, e.g., 3-6 months) reduction of intraocular pressure. In general, the biodegradable polymer material of an implant of this invention may constitute from 1% to 99% of the implant by weight (% w/w). In some embodiments, the biodegradable polymer material represents 80% to 99% of the implant by weight (% w/w). In some embodiments, the biodegradable polymer material represents about 92% to about 99% of the implant by weight.

In one embodiment, the biodegradable polymer material comprises or consists of first, second, and third biodegradable polymers. The first and second polymers may be poly(D,L-lactide) polymers that differ one from the other by their end group (ester or acid) and/or their inherent viscosity (as determined for a 0.1% solution in chloroform at 25° C.); and the third polymer may be a poly(D,L-lactide-co-glycolide). The implant may optionally further comprise hexadecanol.

In one embodiment, the first polymer is a poly(D,L-lactide) having an ester end group and an inherent viscosity of 0.25-0.35 dl/g (as measured for a 0.1% w/v solution in chloroform at 25° C.) (e.g., R203S); the second polymer is a poly(D,L-lactide) having an acid end group (i.e., a carboxyl end group) and an inherent viscosity of 0.25-0.35 dl/g (as measured for a 0.1% w/v solution in chloroform at 25° C.) (e.g., R203H); and the third polymer is a poly(D,L-lactide-co-glycolide) having an ester end group, an inherent viscosity of 0.16-0.24 dl/g (as measured for a 0.1% w/v solution in chloroform at 25° C.), and a D,L-lactide:glycolide ratio of about 75:25 (e.g., RG752S).

In some embodiments, the first, second, and third biodegradable polymers are independently selected from the group consisting of:

R202H, which is a poly(D,L-lactide) having an acid end group and an inherent viscosity of 0.16-0.24 dl/g, as measured for a 0.1% solution in chloroform at 25° C.;

R203H, which is a poly(D,L-lactide) having an acid end group and an inherent viscosity of 0.25-0.35 dl/g, as measured for a 0.1% solution in chloroform at 25° C.;

R202S, which is a poly(D,L-lactide) having an ester end group and an inherent viscosity of 0.16-0.24 dl/g, as measured for a 0.1% solution in chloroform at 25° C.

R203S, which is a poly(D,L-lactide) having an ester end group and an inherent viscosity of 0.25-0.35 dl/g, as measured for a 0.1% solution in chloroform at 25° C.; and RG752S, which is a poly(D,L-lactide-co-glycolide) having an ester end group and an inherent viscosity of 0.16-0.24 dl/g (as measured for a 0.1% solution in chloroform at 25° C.), and a D,L-lactide:glycolide molar ratio of about 75:25.

In one embodiment, the first polymer is a poly(D,L-lactide) having an ester end group and an inherent viscosity of 0.25-0.35 dl/g, the second polymer is a poly(D,L-lactide) having an acid end group and an inherent viscosity of 0.16-0.24 dl/g, and the third polymer is a poly(D,L-lactide-co-glycolide) having an ester end group and an inherent viscosity of 0.16-0.24 dl/g and a D,L-lactide:glycolide ratio of about 75:25, where the inherent viscosity of each polymer or copolymer is measured for a 0.1% solution of the polymer or copolymer in chloroform at 25° C.

In one specific embodiment, the first polymer is R203S, the second polymer is R202H, and the third polymer is RG752S, and the implant further comprises the excipient hexadecan-1-ol. In specific forms, the implant comprises from 0.001% to 10% by weight of the hexadecan-1-ol.

In another embodiment, the biodegradable polymer material comprises or consists of first and second biodegradable polymers, wherein the first polymer is a poly(D,L-lactide) having an ester end group and an inherent viscosity of 0.25-0.35 dl/g (as measured for a 0.1% w/v solution in chloroform at 25° C.) (e.g., R203 S) and the second polymer is a poly(D,L-lactide) having an acid end group (i.e., carboxyl) and an inherent viscosity of 0.25-0.35 dl/g (as measured for a 0.1% w/v solution in chloroform at 25° C.) (e.g., R203H).

In another embodiment, the biodegradable polymer material comprises or consists of a poly(D,L-lactide) having an acid end group (i.e., a carboxyl end group) and an inherent viscosity of 0.16-0.24 dl/g (as measured for a 0.1% w/v solution in chloroform at 25° C.) (e.g., R202H).

In another embodiment, the biodegradable polymer material comprises or consists of a poly(D,L-lactide) having an acid end group (i.e., carboxyl end group) and an inherent viscosity of 0.25-0.35 dl/g (as measured for a 0.1% w/v solution in chloroform at 25° C.) (e.g., R203H).

One embodiment is a biodegradable intraocular implant comprising a biodegradable polymer material, hexadecan-1-ol, and about 40% by weight of the Solid Complex, wherein the compound and the hexadecane-1-ol are associated with the biodegradable polymer material, and wherein the biodegradable polymer material comprises i) a poly(D,L-lactide) having an ester end group and an inherent viscosity of about 0.25-0.35 dl/g, ii) a poly(D,L-lactide) having an acid end group and an inherent viscosity of about 0.16-0.24 dl/g, and iii) a poly(D,L-lactide-co-glycolide) having an ester end group, an inherent viscosity of about 0.16-0.24 dl/g, and a D,L-lactide:glycolide ratio of about 75:25, wherein the inherent viscosity of each poly(D,L- lactide) and poly(D,L-lactide-co-glycolide) as given above is measured for a 0.1% solution of the polymer in chloroform at 25° C. In some embodiments, the implant is an extruded implant. In one embodiment, the implant further comprises an antioxidant, a chelating agent, or both an antioxidant and a chelating agent. In specific forms the antioxidant is butylated hydroxyanisole or ascorbic acid and the chelating agent is EDTA. The intraocular implant may be sized for placement in the anterior chamber of the eye.

Another embodiment is an intraocular implant comprising about 40% by weight of Solid Complex, and about 5.6% by weight hexadecan-1-ol, about 50.3% by weight R203S, which is a poly(D,L-lactide) having an ester end group and an inherent viscosity of about 0.25-0.35 dl/g, about 22.4% by weight RG752S, which is a poly(D,L-lactide-co-glycolide) having an ester end group and an inherent viscosity of about 0.16-0.24 dl/g and a D,L-lactide:glycolide ratio of about 75:25, about 11.2% by weight R202H, which is a poly(D,L-lactide) having an acid end group and an inherent viscosity of about 0.16-0.24 dl/g, about 2.0% by weight butylated hydroxyanisole, and about 0.5% by weight EDTA, wherein the inherent viscosities of the R203S, R202H, and RG752S polymers correspond to those measured for a 0.1% solution of the polymer in chloroform at 25° C.

Implants according to any of the embodiments listed above may preferably comprise at least about 5% but no more than about 75% of the Solid Complex by weight. For example, the Solid Complex may be present in the implant in an amount of between 40 and 60% by weight of the implant.

Implants comprising a biodegradable polymer material of the type described above may provide for a constant, steady release of the Solid Complex for extended periods, such as 3 months, 4-5 months, or for 6 months.

PLA and PLGA polymers from the RESOMER® polymer product line are available from Evonik Industries AG, Germany.

Various techniques may be employed to make the intraocular implants described herein. Useful techniques may include extrusion methods (for example, hot melt extrusion) to produce rod-shaped implants (or fibers), compression methods to produce tablets, wafers, or pellets, and solvent casting methods to produce biodegradable sheets, films, and dry powders. Emulsion methods to produce a plurality of microspheres may also be of use in preparing a biodegradable intraocular drug delivery system for the sustained release of the Solid Complex into an eye in a patient. Accordingly, one embodiment provides for a pharmaceutical composition suitable for placement in an ocular region of an eye and comprising a plurality of biodegradable microspheres encapsulating the Solid Complex.

An extruded implant can be made by a single or double extrusion method, and may be made with a piston or twin screw extruder, for example. Choice of technique, and manipulation of technique parameters employed to produce the implants can influence the release rates of the drug. Extrusion methods may allow for large-scale manufacture of implants and result in implants with a progressively more homogenous dispersion of the drug within a continuous polymer matrix, as the production temperature is increased. Extrusion methods may use temperatures of from about 60° C. to about 150° C., or from about 70° C. to about 100° C., or lower as necessary.

In one embodiment, an intraocular implant according to the present invention is produced by an extrusion process. Polymers and excipients, if any, are generally blended with the therapeutic agent, and then co-extruded at a selected temperature to form a filament comprising a biodegradable polymer matrix (or material) and the therapeutic agent dispersed within and/or distributed throughout the matrix (or material). If desired the filament may be pulverized and re-extruded to form a double extruded implant.

In one variation of producing implants by an extrusion process, the therapeutic agent, biodegradable polymer(s), and, optionally, one or more excipients are first mixed at room temperature (blended in a container) and then heated to a temperature range of 60° C. to 150° C., for a time period of between 1 and 60 minutes, such as 1 to 30 minutes, 5 minutes to 15 minutes, or 10 minutes. The mixture is then extruded through a nozzle at a temperature of 60° C. to 130° C., or at 75° C. The extruded filament is then cut to desired lengths to produce intraocular implants having a specific weight. The orifice of the nozzle through which the mixture is extruded will generally have a diameter appropriate to the desired diameter of the implant, but if necessary the extruded filament can be pulled from the nozzle to further reduce the diameter of the implant. The extruded implant may be generally cylindrical or non-cylindrical, having a length and diameter (or other dimension as appropriate to non-cylindrical fibers) suitable for placement in an ocular region of the eye such as the anterior chamber or vitreous body.

One possible method for producing an intraocular implant of the present disclosure uses a combination of solvent casting and hot melt extrusion. See, for example, US 2010/0278897. In this method, a dry powder or film is first prepared by dissolving all materials (active agent, polymer(s), and excipients, if any) in an appropriate solvent, such as ethyl acetate, to form a solution. The solution is then cast into a suitable container (e.g., a TEFLON® dish), and then dried in a vacuum oven overnight to form a dry film. The film is then ground into particles, which are collected and extruded by hot melt extrusion (using, for example, a piston extruder) to prepare a filament containing the active agent and one or more biodegradable polymers. The filament may be cut to a length and thereby weight suitable for placement in the eye. The extrusion temperature for this process may range from 45° C. to 85° C.

An extruded filament or implant cut from an extruded filament may be terminally sterilized with electron beam (ebeam) radiation. An effective dose of ebeam radiation may be 20-30 kGy, or more specifically 25 kGy.

More information on intracameral implants and methods for making the implants can be found, for example, in U.S. Pat. No. 8,647,659 and in U.S. Pat. No. 9,289,413, which are incorporated by reference herein. For example, the technique of hot melt extrusion can be used to make the implants, and is incorporated by reference herein.

In some embodiments of the method, the pharmaceutical composition is for ophthalmic application. In some embodiments of the method, the pharmaceutical composition is in the form of a solution for ophthalmic application.

For ophthalmic application, the solution is prepared using a physiological saline solution as a major vehicle. The pH of such ophthalmic solutions should for example be maintained from 4.5 to 8.0 with an appropriate buffer system, a neutral pH being preferred but not essential. The formulations may also contain conventional, pharmaceutically acceptable preservatives, stabilizers and surfactants.

Exemplary preservatives that may be used in the pharmaceutical compositions include, but are not limited to, benzalkonium chloride, chlorobutanol, thimerosal, phenylmercuric acetate and phenylmercuric nitrate. Likewise, various preferred vehicles may be used in the ophthalmic solution preparations. These vehicles include, but are not limited to, polyvinyl alcohol, povidone, hydroxypropyl methyl cellulose, poloxamers, carboxymethyl cellulose, hydroxyethyl cellulose, cyclodextrin and purified water. The ophthalmic solution preparation may also include a surfactant; however, surfactants are not necessary as surfactants are added to formulations to dissolve or increase solubility of the drug in formulation vehicles.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present disclosure includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. Exemplary chelating agent is edetate disodium, although other chelating agents may also be used in place of or in conjunction with it.

The ingredients are usually used in the following amounts: Ingredient Amount (% w/w) active ingredient about 0.001-5, preservative 0-0.10, vehicle 0-40, tonicity adjustor 0-10, buffer 0.01-10, pH adjustor q.s. pH 4.5-7.5, antioxidant as needed surfactant as needed, purified water as needed, to make 100%.

The ophthalmic formulations of the present invention can be conveniently packaged in forms suitable for metered application, such as in containers equipped with a dropper, to facilitate application to the eye. Containers suitable for drop wise application are usually made of suitable inert, non-toxic plastic material, and generally contain between about 0.5 and about 15 ml solution. One package may contain one or more unit doses.

Especially preservative-free solutions are often formulated in non-resalable containers containing up to about ten, such as up to about five units doses, where a typical unit dose is from one to about 8 drops, such as from one to about 3 drops. The volume of one drop usually is about 20-35 μl.

EXAMPLES

The following examples are illustrative in nature and are in no way intended to be limiting.

Example 1: Preparation and Characterization of the Solid Complex for Stability Studies One method by which the Solid Complex was prepared is described below.

In particular, to a 20-mL glass vial containing γ-Cyclodextrin (973.67 mg) was added 15 mL distilled water. Applying sonication, a clear solution was obtained. To the solution was added 346.13 mg of Compound 1 which was originally stored in −20° C. freezer, and then equilibrated at R.T. for 30 minutes and vortexed. Within a few minutes, the suspension turned from light to white suspension. The vial was placed onto EnviroGenie shaker for end-over-end rotation at 8 rpm and 25° C. After 24 hours, the white milky suspension was transferred into a 50 mL centrifuge tube. Centrifugation was performed at 5250 g for 15 minutes at 20° C. Then the supernatant was decanted to another glass vials. 1 mL of the supernatant was diluted with acetonitrile (DF=2) and stored it in −20° C. freezer. Ultracentrifugation was run (60,000 g/20° C./15 minutes) on the 1 mL of above supernatant. The obtained supernatant was diluted with acetonitrile (DF=2) and stored it in −20° C. freezer.

The white solids isolated after centrifugation at 5,250 g for 15 minutes at 20° C. were placed in a fume hood for drying at ambient conditions. After three days, vacuum drying was applied on the white solids at ambient temperatures to obtain the Solid Complex (1.01 g).

After air drying for three days and before vacuum drying, approximately 3-5 mg of the white solids was subject to XRPD analysis under conditions listed below: Rigaku Miniflex, Zero background sample plates, Scan range: 3-45° (2θ), Scan rate: 1° (2θ)/minute, Step size: 0.05°, Cu Kα, λ=1.54 Å, 30 kV/15 mA. See FIG. 1A for the XRPD. In addition, see FIG. 10 for an overlay of an XRPD of un-complexed compound 1 (Form A and Form B), gamma cyclodextrin (γ-CD), and the Solid Complex.

The sample subjected to XRPD was studied by TGA/DSC under the conditions below. See FIG. 2A-2C for TGA/DSC of Compound 1, γ-cyclodextrin, and the Solid Complex.

| Analysis | Condition |
|---|---|
| TGA | TA Q5000IR, R.T. to 350° C. at 10° C./min |
| DSC | TA Q2000, 20 to 250° C. at 10° C./min., non-hermetic pan |

About 10 mg of the Solid Complex after air drying but before vacuum drying was heated to 150° C. at 10° C./min. The solids were subjected to XRPD analysis under conditions described in the immediately above paragraph. See FIG. 3A for the XRPD, which indicated that the Solid Complex turned into amorphous after being heated to 150° C. at 10° C./min. However, the Solid Complex still remained solid, whereas various un-complexed crystalline forms of Compound 1 melted between about 40 and about 60° C. (see Example 4).

Example 2: Stability Study of the Solid Complex

The Solid Complex prepared from Example 1 (the batch of 1.01 g which is after vacuum drying) and Compound 1 were weighed into separate 2 ml HPLC vials according to the table below:

| | Time point | | | | | |
|---|---|---|---|---|---|---|
| Sample | Time 0 | Week 1 | Week 2 | Week 4 | Week 8 | Week 12 |
| Compound 1 (mg) | 1.280 (white solid) | 2.103 | 1.303 | 1.154 | 1.533 | 1.692 |
| Solid Complex (mg) | 3.976 (white solid) | 2.683 | 2.329 | 2.410 | 2.587 | 2.322 |

All the vials were sealed with HPLC vial cap. The Time 0 samples were in −20° C. freezer and all other samples in 40° C./75% RH chamber. At predetermined time points, samples of Compound 1 were dissolved with solvent mixture #1 (1 mL ACN+0.5 mL MeOH) and samples of the Solid Complex were dissolved with solvent mixture #2 (1 mL water+0.5 mL MeOH). After appropriate dilution, analyzed the samples by HPLC according to the method below:

| | |
|---|---|
| Column: | ACE 3 C18 (75 × 4.6 mm 3 µm; Mac Mod, P/N ACE-111-7546) |
| Mobile Phase A: | 50/25/25 water/ACN/MeOH, v/v/v (with 0.01% TFA) |
| Mobile Phase B: | 50/50 ACN/MeOH, v/v/v (with 0.01% TFA) |
| Pump Mode: | Gradient |
| Needle Wash: | 50/50 water/ACN, v/v |
| Seal Wash: | 90/10 water/ACN, v/v |
| Flow Rate: | 1.0 mL/min |
| Column Temperature: | 30° C. |
| Autosampler Temperature: | Not applicable |
| Injection Volume: | 20 µL |
| Detector Wavelength: | 240 nm |
| Run Time: | 45 minutes |

| Time (mm) | % A | % B | Curve |
|---|---|---|---|
| 0.0 | 100 | 0 | — |
| 13.0 | 100 | 0 | 6 |
| 28.0 | 0 | 100 | 6 |
| 35.0 | 0 | 100 | 6 |
| 35.1 | 100 | 0 | 6 |
| 45.0 | 100 | 0 | 6 |

The standard stock solution of Compound 1 was prepared by dissolving 1.18 mg Compound 1 with 25 ml mixture of acetonitrile and water (acetonitrile:water=1:1). The stock solution was serially further diluted with a dilution factor of 2 to obtain a standard calibration curve.

Results: at predetermined time points, the appearance of the samples were summarized in the table below. FIG. 7 shows the time profile of Compound 1 and Solid Complex.

| | Time Point | | | | | |
|---|---|---|---|---|---|---|
| | 0 | Day 1 | Week 1 | Week 2 | Week 4 | Week 8 | Week 12 |
| Compound 1 | White powder | Oil | Oil | Oil | Oil | Oil | Oil |
| Solid Complex | White powder | White powder | White powder | White powder | White powder | White powder | White powder |

Thus, as shown above, when stored at 40° C./75% RH, Compound 1 seemed to be both physically and chemically more stable when encapsulated in solid complex with γ-cyclodextrin, while un-complexed Compound 1 became an oil. In addition, un-complexed Compound 1 lost about 20% potency at the end of the 12-week study, the Solid Complex remained as solids and only lost about 7% potency.

Example 3: Solid Complex Formation with Gamma-Cyclodextrin in Comparison with Alpha- and Beta-Cyclodextrin Cyclodextrin in different amount according to the tables below was weighed into 2 ml HPLC vial. Distilled water (1 mL) was added into the vial and the vial was vortexed till clear solution was obtained. Excess amount of Compound 1 was added to the solution and the resulting mixture was vortexed to generate white suspension. The vial was placed onto orbital shaker at 500 rpm and room temperature. After 5 days, all the samples with γ-Cyclodextrin became white suspension. All other samples were clear solutions with oil on the bottom of the vials.

| Cyclodextrin (CyD) | Concentration (M) | Calculated CyD (mg) | Weighed CyD (mg) |
|---|---|---|---|
| α-CD (MW = 972.84) | 0.01 | 9.7 | 10.0 |
| | 0.02 | 19.5 | 19.3 |
| | 0.03 | 29.2 | 30.1 |
| | 0.04 | 38.9 | 38.8 |
| | 0.05 | 48.6 | 48.9 |
| | 0.06 | 58.4 | 58.5 |
| β-CD (MW = 1134.98) | 0.006 | 6.8 | 7.0 |
| | 0.008 | 9.0 | 9.3 |
| | 0.01 | 11.3 | 11.7 |
| | 0.013 | 14.7 | 14.9 |
| | 0.016 | 18.1 | 18.4 |
| | 0.02 | 22.7 | 22.7 |
| γ-CD (MW = 1297.12) | 0.01 | 13.0 | 13.4 |
| | 0.02 | 25.9 | 25.9 |
| | 0.03 | 38.9 | 39.2 |
| | 0.04 | 51.9 | 51.9 |
| | 0.05 | 64.9 | 65.0 |
| | 0.06 | 77.8 | 78.0 |

Only the sample with γ-Cyclodextrin generated white solids. After centrifugation at 18000 g(rcf) for minutes, the wet solids on the bottom of the micro centrifuge tube were applied on zero background XRPD sample plates and subjected to XRPD scan on a Bruker D8 Discover System under the following conditions: Bruker D8 Discover with a GADDS detector (PILOT); Zero background sample plates; Scan range: 6-45° (2θ); Step size: 0.02° (2θ); No. of frames: 3; Scan time per frame: 8 minutes; Cu Kα, λ=1.54 Å, 40 kV/40 mA. This sample of the Solid Complex was crystalline. See FIG. 1B for the XRPD.

The solids on the XRPD sample plate were studies by TGA/DSC under the following conditions:
TGA: TA Q5000IR, R.T. to 350° C. at 10° C./min.
DSC: TA Q2000, 20 to 250° C. at 10° C./min., non-hermetic pan
See FIG. 2C' for the TGA/DSC.

A sample of the wet solids was divided into two sub-samples:
(1) Subsample #1 was transferred into an amber 2-mL HPLC vial and placed into 50° C. oven for overnight drying;
(2) Subsample #2 was in the original micro centrifuge tube. The tube was subjected to vacuum at ambient temperatures for overnight drying.

Figure 3B:
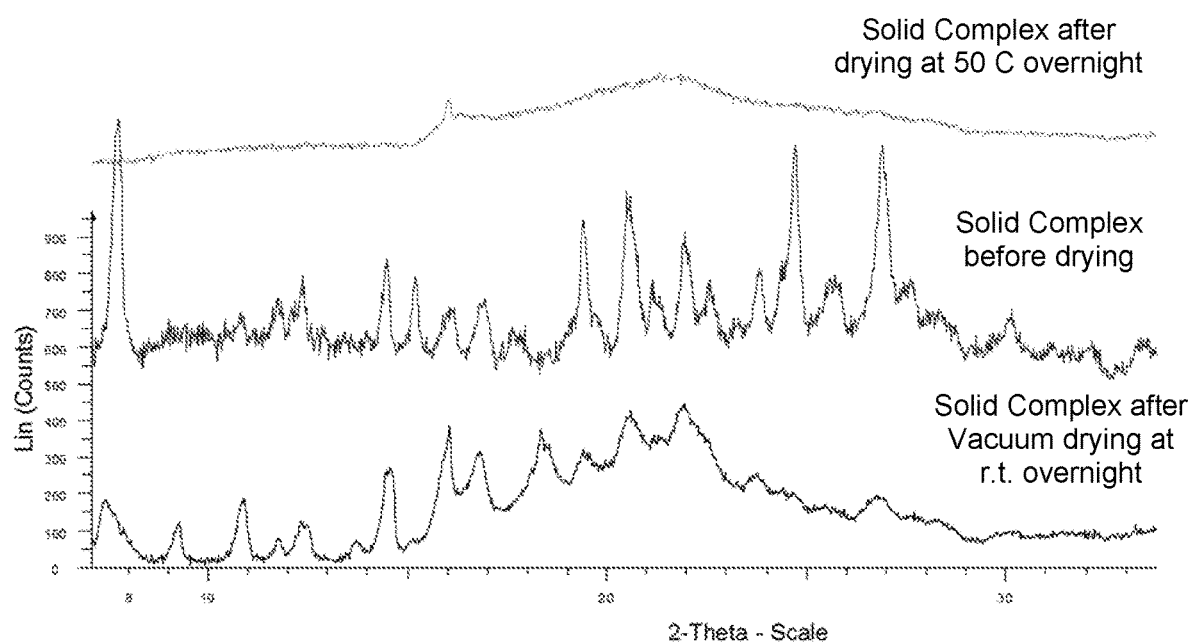
FIG. 3B shows XRPDs of the Solid Complex obtained from Example 3 before and after drying.
Figure 4:
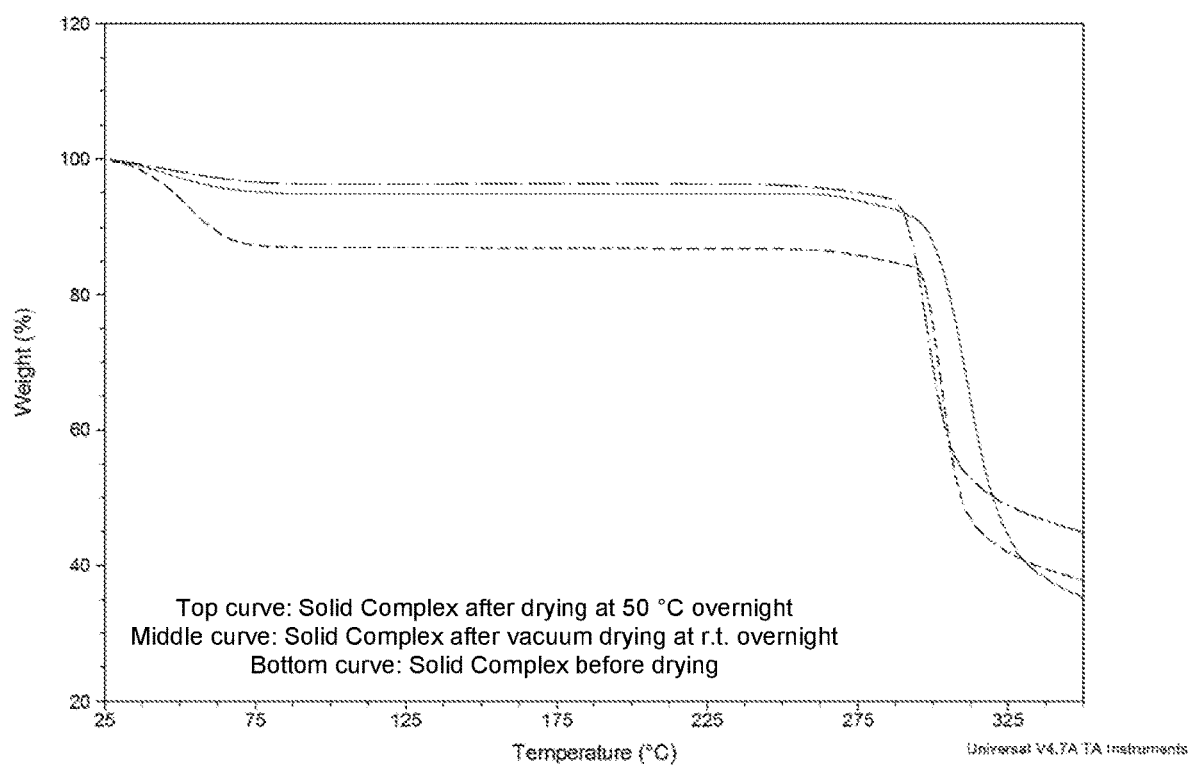
FIG. 4 shows TGA of the Solid Complex obtained from Example 3 before and after drying.
Figure 5:
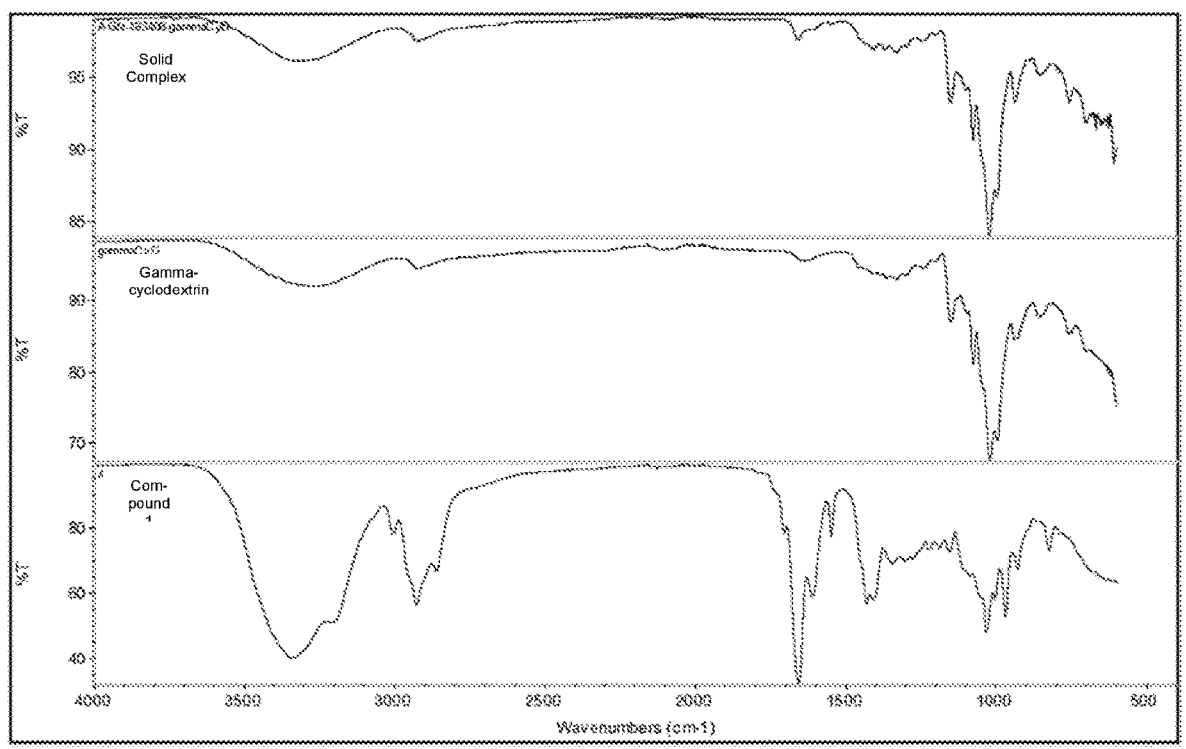
FIG. 5 shows FTIR of the Solid Complex obtained from Example 3, gamma-cyclodextrin, and Compound 1.
Figure 6:
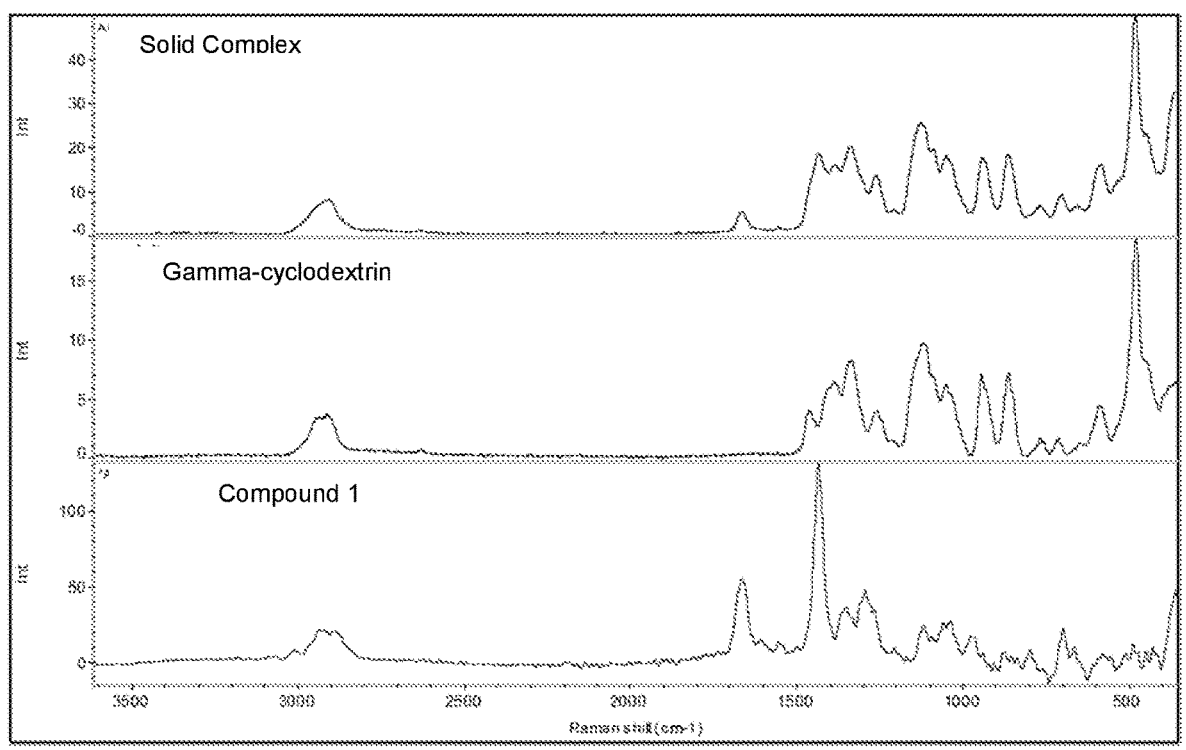
FIG. 6 shows Raman of the Solid Complex obtained from Example 3, gamma-cyclodextrin, and Compound 1.
Figure 8:
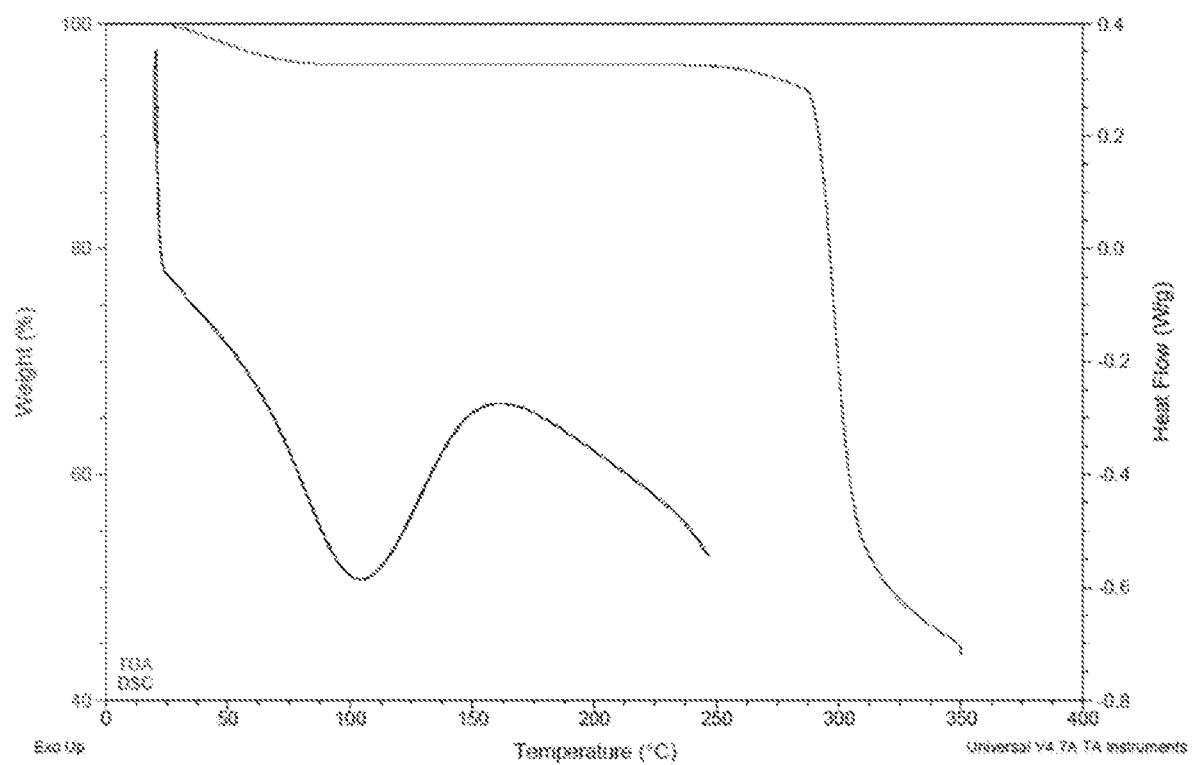
FIG. 8 shows TGA and DSC of the Solid Complex obtained from example 3 after drying at 50° C. overnight.
Figure 9:
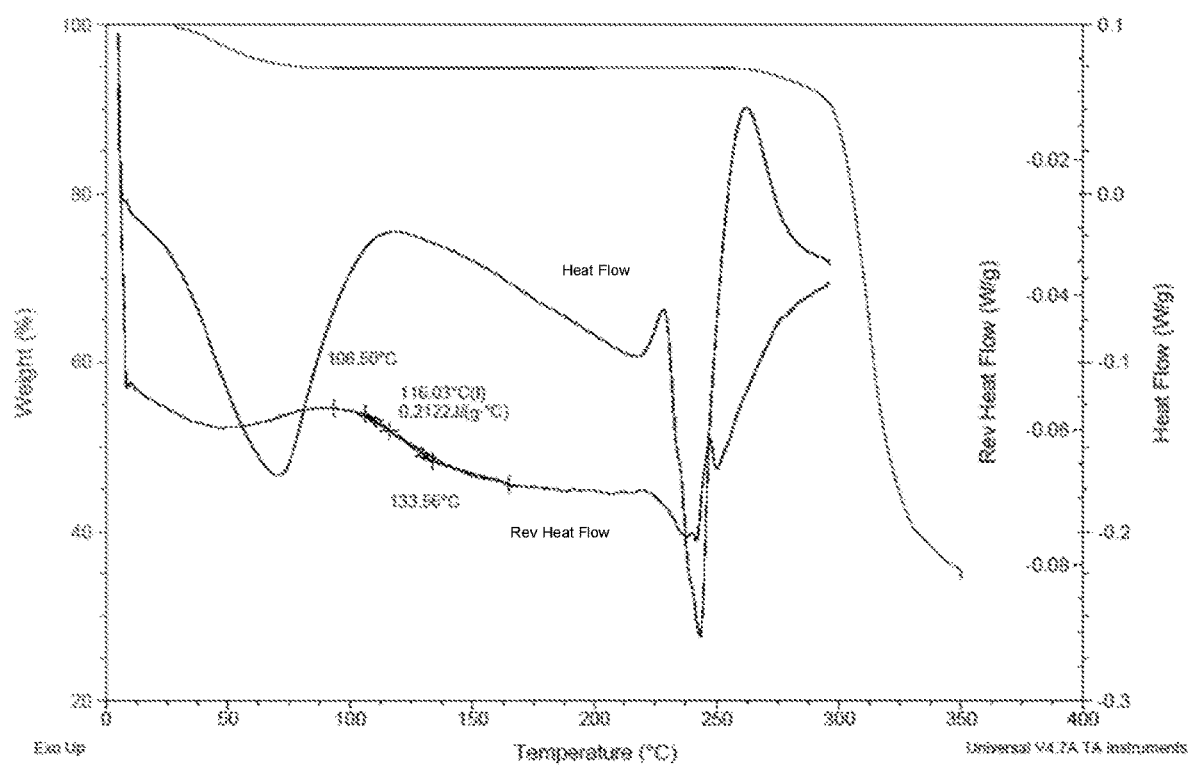
FIG. 9 shows TGA and DSC of the Solid Complex obtained from example 3 after vacuum drying at room temperature overnight.

The above two samples were further characterized by the following techniques:
1. XRPD (see method described above). See FIG. 3B
2. TGA (R.T. to 350° C. at 10° C./min.) See FIG. 4
3. DSC/MDSC (see method described above) (MDSC is modulated DSC, a DSC with modified heating programs in order to separate some overlapping thermal events such as glass transition). See FIGS. 8 and 9. In FIG. 9, total heat flow signal is used in case there is melting peak, reversing heat flow signal is used for defining glass transition temperature.
4. FTIR (ATR, 600-4000 cm$^{-1}$ with a resolution of 4 cm$^{-1}$) See FIG. 5.
5. Raman (780 nm, 10×, 30 sec. per exposure, 2 exposures) See FIG. 6.

XRPD of subsample #1 showed that the Solid Complex lost crystalline after overnight drying at 50° C., however the complex still remained solid. Raman spectra confirmed presence of Compound 1 in the Solid Complex.

Example 4: Preparation of Form a and Form B of Compound 1 and Determination of Melting Points General Data Acquisition
X-Ray Powder Diffraction (XRPD):

The Rigaku Smart-Lab X-ray diffraction system was configured for reflection Bragg-Brentano geometry using a line source X-ray beam. The x-ray source is a Cu Long Fine Focus tube that was operated at 40 kV and 44 mA. That source provides an incident beam profile at the sample that changes from a narrow line at high angles to a broad rectangle at low angles. Beam conditioning slits are used on the line X-ray source to ensure that the maximum beam size is less than 10 mm both along the line and normal to the line. The Bragg-Brentano geometry is a para-focusing geometry controlled by passive divergence and receiving slits with the sample itself acting as the focusing component for the optics. The inherent resolution of Bragg-Brentano geometry is governed in part by the diffractometer radius and the width of the receiving slit used. Typically, the Rigaku Smart-Lab is operated to give peak widths of 0.1° 2θ or less. The axial divergence of the X-ray beam is controlled by 5.0-degree Soller slits in both the incident and diffracted beam paths.

Differential Scanning Calorimetry (DSC):

DSC analyses were carried out using a TA Instruments Q2000 instrument. The instrument temperature calibration was performed using indium. The DSC cell was kept under a nitrogen purge of approximately 50 ml per minute during each analysis. The sample was placed in a standard, crimped, aluminum pan and was heated from 20° C. to 350° C. at a rate of 10° C. per minute.

Melting Point Determinations:

Melting points were determined using a Stuart SMP3 apparatus. Samples were packed into capillary tubes for analysis.

Hot-Stage Microscopy:

Hot-stage microscopy experiments were carried out on a Linkam 1 TS420 temperature controlled stage mounted on a Leica DM 2500 P compound microscope. Images were captured using a QImaging Micro Publisher 3.3 RTV camera. The sample was heated at a rate of 1° C./min.

Crystallization Experiments and Melting Point Determinations

For the preparations shown below, portions of a sample of Compound 1 (which was determined to be Form A by XRPD) were recrystallized in various solvents and under various conditions to prepare Compound 1 Form A for determination of their melting points/ranges. In addition, various other portions of the sample were subjected to additional conditions (see table below) to prepare Compound 1 in Form A and Form B for determination of their melting points/ranges. Selected specific melting ranges are shown for the various preparations in the table below; however, all preparations resulted in solids which melted at between about 40 and about 60° C.

Preparation of Compound 1 Form a from Acetonitrile:

A mixture of 20.2 mg of Compound 1 and 1 ml of dry acetonitrile (from over 3 Å molecular sieves) was heated on a hot plate set at 85° C. until the solid dissolved. the solution was removed from the hot plate and allowed to cool to ambient temperature. During standing at ambient temperature overnight, crystallization occurred. The mixture was placed in a refrigerator (about 5° C.) for 6 days. The liquid was decanted and the remaining solids were dried in a stream of dry air to give 16.5 mg (82% yield) of Compound 1 Form A.

Preparation of Compound 1 Form a from Acetonitrile with Temperature Cycling:

A mixture of 28.7 mg of Compound 1 and 1 ml of dry acetonitrile (from over 3 Å molecular sieves) was heated on a hot plate set at 85° C. until the solid dissolved. the solution was removed from the hot plate and allowed to cool to ambient temperature. During standing at ambient temperature overnight, crystallization occurred. The mixture was placed in a controlled temperature bath and temperature cycled ten times, each cycle entailing cooling from 35° C. to 10° C. over one hour, then heating from 10° C. to 35° C. over one hour. Vacuum filtration afforded 15.5 mg (54% yield) of Compound 1 Form A.

Preparation of Compound 1 Form a from Ethyl Acetate:

A solution of 20.1 mg of Compound 1 in 2 ml of dry ethyl acetate (from over 3 Å molecular sieves) was placed in a vial; and the vial was covered with a piece of aluminum foil containing four pinholes. The vial was placed in a dry box (relative humidity of about 0%) and allowed to stand at ambient temperature for three days, during which time the solvent evaporated to leave Compound 1 Form A.

| Method | Solvents [a] | Conditions | Form | Melting point (° C.)[b] |
|---|---|---|---|---|
| evaporation | EtOAc (dry) | Pinhole closure, dry air purge | A | 47.2-54.0 |
| | | Open vial, dry air purge | A | 50.0-55.6 |
| Cooling | ACN (dry) | Reflux → 5° C. | A | 47.4-55.9 |
| | | Reflux →RT, 10 cycles 35↔10° C. | A | ~40-60[c] |
| | ACN/H2O (1:100) | Reflux →5° C., 10 cycles 35↔10° C. | A | |

-continued

| Method | Solvents [a] | Conditions | Form | Melting point (° C.)[b] |
|---|---|---|---|---|
| Slurry | ACN | RT, 11 days | A | |
| | ACN/H2O (1:100) | RT, 11 days | B | |
| | BuOH/MTBE (1:20) | RT, 10 days | B | 43.4-46.8 |
| | EtOAc | RT, 8 days | A | |

[a] ACN = acetonitrile, BuOH = l-butanol, EtOAc = ethyl acetate, MTBE = tert-butyl methyl ether, RT = room temperature.
[b] Unless otherwise indicated, the melting points were determined on a capillary melting apparatus
[c] Determined on a Linkam hot stage.

As can be seen from the above, Forms A and B (i.e. un-complexed Compound 1), have much lower melting points of between about 40 and about 60° C. than the Solid Complex, which remained solid even above 150° C. (see Example 1) rendering the complex more amenable to, for example, processing through hot-melt extrusion to form solid implants comprising the Solid Complex.

Throughout this specification reference is made to publications such as US and foreign patent applications, journal articles, book chapters, and others. All such publications are expressly incorporated by reference in their entirety, including supplemental/supporting information sections published with the corresponding references, for all purposes unless otherwise indicated.

Various modifications of the present invention, in addition to those shown and described herein, will be apparent to those skilled in the art of the above description. Such modifications are also intended to fall within the scope of the appended claims.

The foregoing description is illustrative of particular embodiments of the invention, but is not meant to be a limitation upon the practice thereof. It should not be construed as limiting the overall scope hereof; rather, the ambit of the present disclosure is to be governed only by the lawful construction of the appended claims.

What is claimed is:

1. A solid complex of (Z)-7-((1R,2R,3R,5S)-2-((S,E)-5-(2,5-dichlorothiophen-3-yl)-3-hydroxypent-1-en-1-yl)-3,5-dihydroxycyclopentyl)hept-5-enamide with γ-cyclodextrin.

2. The solid complex of claim 1, which is crystalline.

3. The solid complex of claim 2, which has an XRPD pattern with peaks at 7.58, 10.68, 14.33, 16.82, 23.82, 26.89, 28.51, 30.06, and 35.13, each of the diffraction angles being ±0.2 degrees (2θ).

4. The solid complex of claim 1, which has an XRPD pattern with peaks at 10.83, 11.72, 12.36, 14.51, 19.42, 20.56, and 26.80, each of the diffraction angles being ±0.2 degrees (2θ).

5. The solid complex of claim 1, which is amorphous.

6. The solid complex of claim 1, wherein the molar ratio of (Z)-7-((1R,2R,3R,5S)-2-((S,E)-5-(2,5-dichlorothiophen-3-yl)-3-hydroxypent-1-en-1-yl)-3,5-dihydroxycyclopentyl)hept-5-enamide versus γ-cyclodextrin is about 1:1.

7. A pharmaceutical composition comprising the solid complex of claim 1 and a pharmaceutically acceptable excipient.

8. The pharmaceutical composition of claim 7, which is in the form of an intraocular implant.

9. The pharmaceutical composition of claim 8, wherein the intraocular implant comprises a biodegradable polymer.

10. The pharmaceutical composition of claim 9, wherein the biodegradable polymer is a homo- or copolymer of D-lactic acid, L-lactic acid, racemic lactic acid, glycolic acid, caprolactone, and combinations thereof.

11. The pharmaceutical composition of claim 9, wherein the biodegradable polymer is a random copolymer of 50/50 PLGA.

12. A method of preparing a pharmaceutical composition comprising combining the solid complex of claim 1 with one or more pharmaceutically acceptable excipients.

13. The method of claim 12, wherein the pharmaceutical composition is in the form of a solution for ophthalmic application.

14. The method of claim 12, wherein the pharmaceutical composition is a solid implant.

15. The method of claim 12, wherein the method further comprises subjecting the combination of the solid complex and one or more pharmaceutically acceptable excipients to hot-melt extrusion.

16. The method of claim 15, wherein the pharmaceutical composition is a solid implant.

* * * * *